United States Patent
Sadri

[11] Patent Number: 5,494,822
[45] Date of Patent: Feb. 27, 1996

[54] ORGAN PERFUSION DEVICE

[75] Inventor: Fereydoon Sadri, Redmond, Wash.

[73] Assignee: Bio-Preserve Medical Corporation, Redmond, Wash.

[21] Appl. No.: 282,674

[22] Filed: Jul. 29, 1994

Related U.S. Application Data

[62] Division of Ser. No. 949,187, Sep. 21, 1992, Pat. No. 5,338,662.

[51] Int. Cl.⁶ ............................ A01N 1/02; C12M 1/36; A61M 31/00
[52] U.S. Cl. ........................ 435/284.1; 604/50; 604/66; 604/67; 417/22; 417/42; 417/43; 435/286.1; 435/286.5; 435/286.6
[58] Field of Search .................... 435/1, 283, 289, 435/291; 604/50, 66, 67; 62/306; 417/22, 42, 43

[56] References Cited

U.S. PATENT DOCUMENTS

| | | | |
|---|---|---|---|
| 3,406,531 | 10/1968 | Swenson et al. | 62/306 |
| 3,490,438 | 1/1970 | Lavender et al. | 417/394 |
| 3,604,419 | 9/1971 | Haifa et al. | 128/227 |
| 3,639,084 | 2/1972 | Goldhaber et al. | 417/394 |
| 3,660,241 | 5/1972 | Michielsen | 195/127 |
| 3,738,914 | 6/1973 | Thorne et al. | 435/1 |
| 3,753,865 | 8/1973 | Belzer et al. | 195/127 |
| 3,772,153 | 11/1973 | De Roissart | 195/127 |
| 3,843,455 | 10/1974 | Bier | 195/127 |
| 3,877,843 | 4/1975 | Fischel | 417/394 |
| 3,881,990 | 5/1975 | Burton et al. | 195/1.7 |
| 3,892,628 | 7/1975 | Thorne et al. | 435/1 |
| 3,914,954 | 10/1975 | Doerig | 62/306 |
| 3,935,065 | 1/1976 | Doerig | 195/1.7 |
| 3,995,444 | 12/1976 | Clark et al. | 62/306 |
| 4,186,565 | 2/1980 | Toledo-Pereyra | 62/30 |
| 4,242,883 | 1/1981 | Toledo-Pereyra | 62/306 |
| 4,299,919 | 11/1981 | Jellinek | 435/283 |
| 4,395,492 | 7/1983 | Rees | 435/283 |
| 4,618,586 | 10/1986 | Walker | 435/1 |
| 4,629,686 | 12/1986 | Gruenberg | 435/1 |
| 4,666,425 | 5/1987 | Fleming | 604/4 |
| 5,051,352 | 9/1991 | Martindale et al. | 435/1 |
| 5,141,847 | 8/1992 | Sugimachi | 435/1 |
| 5,217,860 | 6/1993 | Fahy et al. | 435/1 |
| 5,338,662 | 8/1994 | Sadri | 435/1 |

FOREIGN PATENT DOCUMENTS 125847  11/1984  European Pat. Off. .

OTHER PUBLICATIONS

T.O.P.S. Medical Corp., advertisement, 1987–1988.
Kent Scientific Corporation, Litchfield, CT, "Isolated Heart", 1991 catalog.

*Primary Examiner*—Robert J. Warden
*Assistant Examiner*—N. Bhat
*Attorney, Agent, or Firm*—Townsend and Townsend and Crew

[57] ABSTRACT

Devices and methods for perfusing organs by controlling either the perfusion pressure or the perfusate flow rate. The operator may select either method of perfusion control. Also provided are devices and methods for perfusing multiple organs simultaneously on the same device.

8 Claims, 2 Drawing Sheets

ORGAN PERFUSION DEVICE

RELATED APPLICATION

The present application is a divisional application of Ser. No. 07/949,187, filed, Sep. 21, 1992, now U.S. Pat. No. 5,338,662.

BACKGROUND OF THE INVENTION

The present invention relates generally to organ perfusion devices and techniques of organ perfusion. In particular, the perfusion devices may simultaneously perfuse more than one organ in an independent manner. The perfusion devices may also perfuse organs at either constant perfusion pressure or constant perfusate flow rate, at the discretion of the operator. Methods are provided for simultaneously perfusing multiple organs, perfusing organs on devices capable of regulating both the flow rate and pressure of a perfusate, and measuring the effect of a stimulus, chemical or otherwise, on organ function.

Maintaining viability of animal organs following removal of the organ from the animal's body (ex vivo viability) or during isolation of the organ from the animal's natural circulation is of great importance for medicine, pharmacology, and physiology. Traditionally, excised solid organs have been maintained through a combination of hypothermia and exposure to nutrient solutions. Hypothermia decreases the metabolic activity of cells within the organ. The decreased metabolic activity lowers the cells' demand for nutrients and oxygen while concurrently suppressing the production of toxic waste products. Exposure to nutrient solutions serves two functions. First, the cells of the isolated organ may be exposed to nutrients and/or oxygen. Second, toxic waste products are removed as the solution is washed over or through the organ.

Devices previously used for maintaining ex vivo organ viability have relied on three methods of nutrient solution exposure. In perfusion, the isolated organ is bathed in a nutrient containing culture medium. While this method is effective for bone marrow or other non-solid organ preservation, perfusion does not optimize solid organ preservation as nutrient supply to the interior of the organ relies on diffusion through the more superficial organ tissue.

Perfusion is a method of administering the nutrient solution through the vascular bed of an organ. The nutrient solution is fed into the arterial side of the organ's vascular system. The solution follows the natural circulatory path of the organ and exits the venous side of the organ's circulation. Superfusion combines both perifusion and perfusion of a single organ.

The devices providing perfusion or superfusion of isolated organs regulate the perfusate flow rate or the perfusion pressure, but not both. Organs perfused by devices regulating only the perfusion pressure typically do not have a constant flow of perfusate to the organ. As the blood vessels in the organ dilate or constrict, either naturally or in response to an external stimulus such as hypothermia, the perfusion pressure changes. The perfusion device adjusts the flow rate of the perfusate so as to maintain a constant pressure. As blood vessels constrict, the perfusate flow rate decreases in order to maintain a constant perfusion pressure. Decreasing perfusate flow can cause hypoxia and injury to the isolated organ. As blood vessels dilate, the perfusate flow rate increases to maintain a constant pressure. Increased perfusate flow can cause electrolyte and free water imbalances resulting in edema and functional alterations. Presently available perfusion devices do not provide a means to control both the pressure or flow rate of perfusate into the isolated organ at the discretion of the operator.

Ex vivo viability is of obvious importance for organ transplants. Because the tissue type of transplanted organs must be compatible with the tissue type of the recipient, available organs must often be transported over long distances for long periods of time to reach a compatible recipient. Also, the demand for transplant organs is greater than the supply, necessitating optimized use of limited resources. Organ viability must be optimized during this waiting period to achieve the most effective results. Devices presently employed for organ transplant and preservation neither monitor the physiological state of the transported organ nor respond to organ changes by altering the preservation conditions under which the organ is being maintained. Thus, preventable organ damage may occur during transport. As more diseases are treated by transplantation, especially with fragile organs, optimizing preservation conditions will assume even greater importance.

Also, ex vivo therapies are being developed for the treatment of various diseases. For example, ex vivo lymphocyte stimulation and activation has been employed for the treatment of AIDS-related diseases. Ex vivo therapy may also provide a means to expose an organ to high doses of a therapeutic modality while protecting other organs from the therapy. Cancer chemotherapy is one such example. Solid tumors, such as hepatomas, do not respond well to doses of chemotherapeutic agents that are tolerable to the bone marrow. Ex vivo treatment of the liver could provide very high drug doses to the tumor while sparing the bone marrow. For effective ex vivo treatment, however, the organ must be perfused so as to optimize viability. Hence, the perfusion device must be capable of delivering adequate levels of perfusate to the organ, monitoring the function and viability of the treated organ, and responding to changes in organ function during treatment. Presently available perfusion devices can not monitor and respond to physiological changes in the isolated organs.

Circulatory isolation of organs within the body is also desirable for medical treatment. If an organ can be perfused in isolation while remaining in the body, many of the advantages of ex vivo therapy may be realized with less morbidity. Catheters that selectively occlude blood vessels leading into and out of a solid organ may be used to selectively perfuse the organ with a therapeutic substance. As in ex vivo therapy, high levels of a drug could be delivered to the diseased organ without risking potentially toxic side-effects in other organs. Also like ex vivo therapy, the perfusion device should be capable of delivering adequate levels of perfusate to the organ, monitoring the function and viability of the treated organ, and responding to changes in organ function during treatment. Otherwise permanent damage to the treated organ could occur.

Isolation of organs from the host circulation, either by organ removal or in vivo circulatory isolation, is also valuable for assessing the pharmacological or toxicological effects of compounds on individual organs. Because a single compound can affect many different organ systems it is often difficult to differentiate the direct effect of the compound on the organ from the effect of the other host responses to the compound. Isolation of the organ from the systemic response of the host provides a means to directly measure the effect of the compound on the organ. Physiological responses to naturally occurring compounds can be similarly assessed. Presently available perfusion devices do not provide the monitoring or perfusate regulating capabilities necessary for assessing complex organ functions or optimizing organ viability.

Measurement of an organ's response to physical stimuli, such as hypothermia, blunt trauma, electrical stimulation, and the like, is also best evaluated by isolating the organ. Similar to measurement of chemical effects on an organ, isolation of the organ eliminates the confounding effects of other host responses. For optimal monitoring, perfusion devices must be capable of altering perfusion characteristics, such as pressure, to differentiate organ effects from vascular effects. For example, hypothermia causes vasoconstriction resulting in hypoperfusion of the organ. Because the delivery of oxygen and other nutrients is altered by the vascular response, the changes in organ function could result from either from cellular effects of the external stimulus or the vascular response to the stimulus. Present perfusion devices do not allow differentiation of these factors.

Devices exist which monitor and adjust the condition of cell culture media. See, e.g., U.S. Pat. Nos. 4,618,586 and 4,629,686. Organ perfusion has special requirements not met by cell culture perfusion devices, however. As noted above, constant pressure perfusion can often result in differences in organ perfusion volume. This difference in perfusate volume can affect the organ's viability and function. A device which provides constant flow perfusion would alleviate this problem. Unfortunately, constant flow perfusion is not always appropriate, such as during extreme vasoconstriction or vasodilation. Comparison to other research often requires constant pressure perfusion also. Hence, it would be preferable for perfusion devices to operate under either constant pressure or constant flow. Perfusion devices available in the art can only perfuse by constant pressure or constant flow.

Physiological or pharmacological research also requires that treated or stimulated organs be compared to control organs. Ideally, the control organ receives identical perfusate at the same temperature, pH, $pO_2$, $pCO_2$, etc. Unfortunately, slight variations in perfusate compositions often occur which can alter the normal organ function. Because the baseline functions of the control organ and the test organ are altered by the perfusate differences, it is difficult to accurately interpret test data. A means to deliver perfusate to both organs from the same source would overcome this difficulty and allow for more accurate physiological and pharmacological assessments. Presently available perfusing devices do not fulfill this need.

Even though the test organs and control organs may not be studied under identical conditions, it is necessary to gather both sets of data in modern research. Conducting two sets of tests is time consuming and laborious for laboratory personnel. A device which would study both the test organ and control organ simultaneously would provide a means to increase laboratory productivity and lower the cost of research. In light of the steadily rising cost of research and the increasing scarcity of funding, a means to generate both test data and control data simultaneously is of great importance.

What is needed in the art are perfusion devices which monitor organ function during perfusion, adjust the perfusion conditions to optimize organ viability, provide a means to simultaneously perfuse test organs and control organs with identical perfusate, and are appropriate for in vivo, ex vivo, and in vitro use. Quite surprisingly, the present invention fulfills these and other related needs.

SUMMARY OF THE INVENTION

The present invention provides organ perfusion devices comprising a first fluid conduit fluidly connecting a source of a perfusate to an upstream pump, a second fluid conduit for fluidly connecting the upstream pump to an organ, a means to regulate the pressure of the perfusate in the second fluid conduit, and a means to regulate the flow rate of the perfusate through the second fluid conduit. The means to regulate the pressure of the perfusate and the means to regulate the flow rate of the perfusate may be an upstream sensor and a pump speed control mechanism.

Also provided are devices for the simultaneous perfusion of a plurality of individual organs comprising, one or more upstream pumps equal in number to the number of individual organs being simultaneously perfused, one or more first fluid conduits connecting each pump to a source of a perfusate, and one or more second fluid conduits connecting the arterial system of each individual organ with a single upstream pump, wherein each upstream pump is connected to only one organ.

Methods for perfusing at least one organ to maintain organ viability are also provided. Generally, the methods comprise connecting the arterial system of each organ to separate pumps by means of at least one fluid conduit, which pumps are connected to a source of a perfusate, and administering the perfusate to each organ by independently regulating each pump to adjust the pressure or flow rate of the perfusate in the fluid conduit.

DETAILED DESCRIPTION OF THE SPECIFIC EMBODIMENTS

Figure 1:
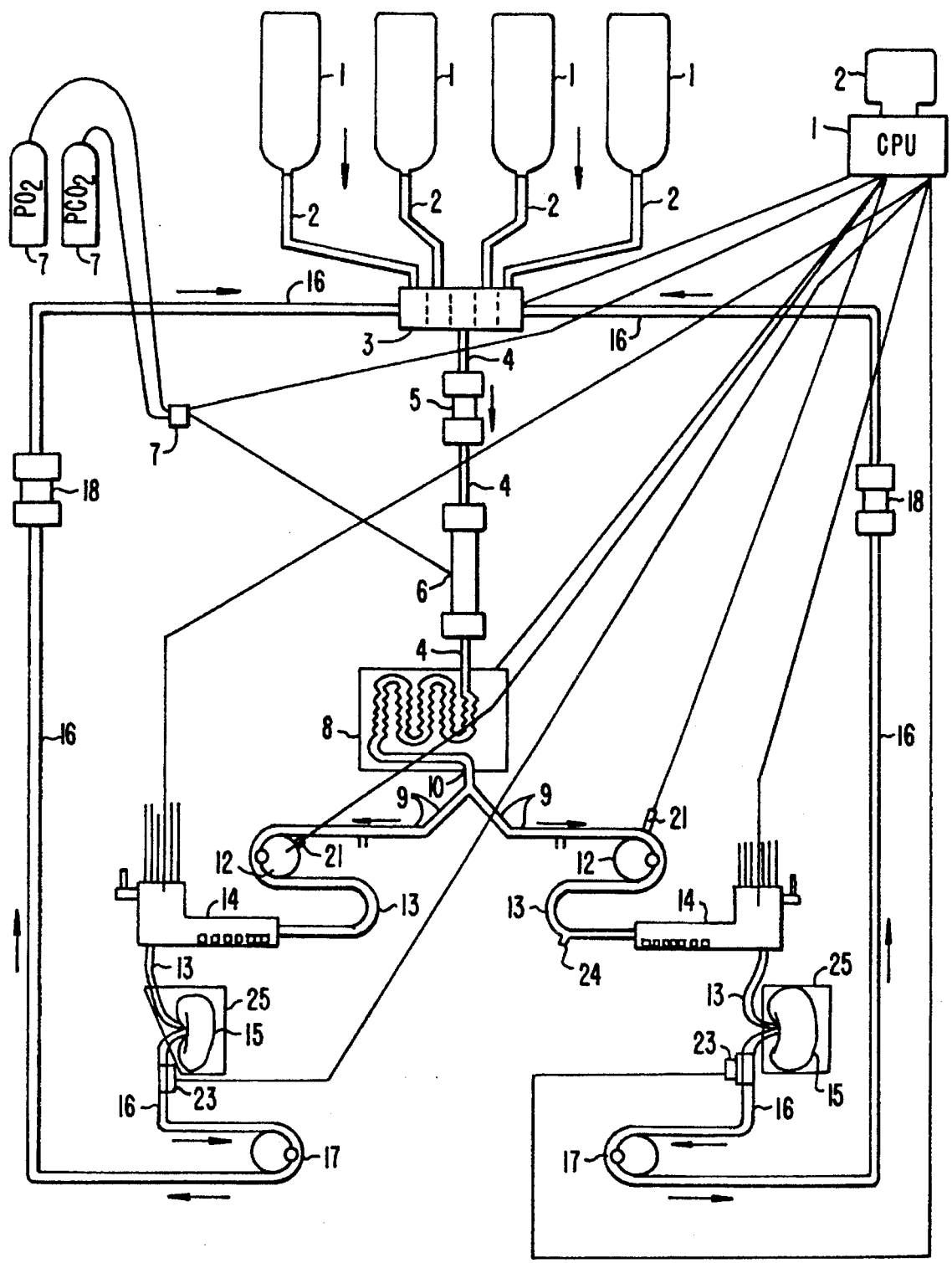
FIG. 1 illustrates a schematic diagram of a perfusion device for perfusing multiple organs constructed in accordance with the principles of the present invention.

According to the present invention, devices and methods are provided for perfusing solid animal organs. Solid organs are those organs which have an identifiable vascular system for carrying blood with separate inflow and outflow vessels. Solid organs which may be perfused by the present invention include hearts, kidneys, livers, thyroids, lungs, intestines, pancreases, reproductive organs, brains, spleens and the like. The organs of any animal may-be perfused, provided that the vascular inflow vessel is of sufficient size to accommodate a fluid conduit. The organ source will generally be mammalian, such as mouse, rat, dog, cat, or human, although other animal species may be appropriate for different applications.

One embodiment of the present invention provides an organ perfusion device having a source of a perfusate, a first fluid conduit fluidly connecting the source of a perfusate to an upstream pump, a second fluid conduit for fluidly connecting the upstream pump to an organ, a means to regulate the pressure of the perfusate in the second fluid conduit, and a means to regulate the flow rate the perfusate through the second fluid conduit.

As used herein, when component A is "upstream" or "proximal" to component B, unrecycled fluid from the source of the perfusate flows through component A before flowing through component B during the normal operation of devices of the present invention. Likewise, component B is "distal" or "downstream" of component A when unrecycled fluid from the source of the perfusate flows through component B after flowing through component A during the normal operation of the devices of the present invention.

The source of a perfusate is not critical and may vary. Typically the source will include at least one reservoir capable of holding fluids. Generally about 4 reservoirs are employed, although this is not critical and may vary. The reservoirs may be glass, stainless steel, plastic or the like. The reservoirs may be closed and sterilized as appropriate. Likewise, the perfusates may be sterile, such as commercially available Ringers Lactate, normal saline, plasma, high oxygen transference solutions, anticoagulated whole blood or components thereof, or the like. For selected applications, such as ex vivo high dose radiation therapy, the patient may be the perfusate source. In this instance, whole blood, anticoagulated with sodium citrate, heparin or the like may serve as the perfusate. Other perfusate solutions are well known in the art.

Multiple reservoirs may be employed, each containing a different fluid. The fluids may be mixed in a predetermined ratio producing a perfusate mixture of a desired composition. During perfusion, the composition of the perfusate may be varied by altering the ratio of the different component fluids in the mixture. For example, one fluid may contain sodium bicarbonate ($NaHCO_2$). The pH of the perfusate mixture can be altered by varying the amount of $NaHCO_2$ fluid in the mixture. If an organ becomes acidotic during perfusion, the perfusate mixture can be adjusted, to increase the $NaHCO_2$ concentration thereby correcting the acidosis.

When multiple reservoirs are employed, a mixing means to selectively mix the fluids from the different reservoirs is employed. By "selectively mix" it is meant that the fluids are mixed in selected volumetric ratios. The volumetric ratios may be predetermined and constant or may be altered during perfusion. Typically, the volumetric ratios are altered in response to changes in organ function in order to optimize organ viability. A fluid conduit connects the reservoirs to the mixing means. By "fluid conduit", it is meant any means of directing the fluid from one component of the device to another component of the device which, except for the proximal and distal openings which connect to the device components, is closed. While generally the fluid conduit means will be tubing, such as polyethylene, silicone, or Tygon® tubing, alternative means are also envisioned, e.g., bored channels through solid supporting structures.

Conveniently the mixing means may be an electronic valve, such as the Cavro Electric Motor Valve, Cavro Corporation. Other mixing means are acceptable, e.g., the device described in U.S. Pat. No. 4,629,686, incorporated herein by reference. Persons of skill in the art will readily appreciate that different valves are appropriate for different uses depending on the size of the organ being perfused, viscosity of the perfusate, cellular content of the perfusate, etc. The electronic valve independently controls the flow rate of each different fluid into a common flow line such as polyethylene, silicone, or Tygon® tubing, or the like. The electronic valve may be controlled directly by the operator or through electronic means, such as a computer which alters the composition of the perfusate mixture in response to externally created signals. Alternatively, the mixing means may be a manual valve device.

After mixing has occurred, or directly from a single reservoir as appropriate, the perfusate may flow through filters, an oxygenator, and/or a heat exchanger, all connected by fluid conduits. The filters may also include a one way valve to avoid backflow into the reservoirs. Suitable filters include, e.g., The Whatman 6702-3600 or Gilman 12158.

The oxygenator may be a membrane oxygenator, such as Sci. Med Ultrox I, and the like, or a hollow fiber oxygenator, such as CD Medical Oxy 10 and Oxy 1 or Unisyn Fibertec Cell-Farm Hollow Fibers Oxygenator and the like. The gas introduced by the oxygenator will generally be $O_2$, $CO_2$, or a mixture thereof. The pH of the perfusate may be adjusted by altering the $CO_2$ content of the perfusate. As the $CO_2$ content increases carbonic acid is formed, lowering the pH of the perfusate. Organ ischemia may be treated by increasing the $O_2$ content of the perfusate.

Typically, the oxygenator is placed in close proximity to the perfused organs. As the perfusate flows through conduits toward the organ, the temperature and other characteristics may change. As the perfusate warms, gasses introduced by the oxygenator may leave solution and form bubbles. The bubbles can then embolize in the organ causing infarction. Situating the oxygenator proximally near the perfused organs limits the risk of bubble embolization. A bubble trap may be placed between the oxygenator and the perfused organ if required, especially in therapeutic applications.

The heat exchanger may serve to cool or warm the perfusate. Cooling is generally preferred for organ preservation, as described in "Basic Concepts in Organ Procurement, Perfusion and Preservation for Transplantation", Ed. Luis H. Toledo-Pereya, Acad. Press 1982, incorporated herein by reference. Ex vivo therapy may employ warmed solutions in order to warm the organ to supraphysiological temperatures, as desired. The heat exchanger also provides a means to determine the effect of environmental temperature changes on organ function. As explained above, the heat exchanger is typically placed proximally near the perfused organs to avoid heat transfer prior to entering the organ.

Upon exiting the source, the perfusate is channeled into a pump through a first fluid conduit. The pump is preferably a roller type pump, such as those employing Master Flex Pump 7018-20, so as to minimize cell lysis when cellular perfusates are employed. A heater circulating pump may be used in lieu of separate heat exchangers and pumps in some embodiments. Generally, the pump will be electrical, although for in vivo perfusion a pneumatic type pump may be preferred to reduce the risk of electrical injury to the organ or patient. The pump propels the perfusate into a second fluid conduit.

The output of the pump is determined by pump speed. The pump speed is regulated in two modes, perfusion pressure or perfusate flow rate in the second fluid conduit. During perfusion, the perfusion pressure or the perfusion flow rate may be varied or held constant. The mode may also be changed, either during perfusion or otherwise. Hence, the pump speed may be changed in response to functional characteristics of the organ or regulated to a constant flow or a constant pressure. When controlled by a computer, the pump speed may be controlled so as to provide either constant perfusion pressure or constant flow rate, provided the uncontrolled mode remains within a defined range. If the uncontrolled mode leaves the predetermined range, the controlled mode will be adjusted. For example, if the organ is being perfused at a constant perfusion pressure, the flow rate may be programmed so as to not decrease below a certain level. If the organ vasoconstricts and the flow rate decreases below the allowed level, the perfusion pressure will be increased to maintain the minimum allowable flow rate.

The pump speed is controlled by a pump speed control mechanism. The pump speed control mechanism will generally be responsive to inputs from a computer or other electronic source. Inputs from the electronic source controls the pump speed control mechanism which in turn controls the speed of the pump. In this way, the pump output is controlled by inputs to the pump speed mechanism. Alternatively, the pump speed control mechanism may be responsive to manual inputs.

After exiting the pump, the perfusate is channeled into a second fluid conduit to the organ. The second fluid conduit terminates in the arterial system of the organ. Generally, the second fluid conduit communicates directly with the main artery of the organ, e.g., the renal artery in human kidneys, the testicular artery in human testes, etc. In organs having a plurality of arterial inputs or accessory circulation, e.g., the human heart, human lung, etc., each arterial input may be perfused from the pump by way of branching the second fluid conduit or by perfusing one artery while appropriately occluding all other entering arteries.

The second fluid conduit may include an upstream sensor. Typically, the upstream sensor may monitor several characteristics of the perfusate in the second conduit prior to entry into the organ. Perfusate characteristics which may be measured include temperature, pH, electrolyte concentration, pressure, flow rate, $pO_2$, $pCO_2$, and the like. Any electrolyte may be measured such as Na, K, Ca, Cl, $NaHCO_2$, Mg, $PO_4$, or the like. Typically surface field effect sensors, such as Micro Electrode Sensors will be employed, although other sensors are acceptable.

The upstream sensors may be microsensors capable of insertion into the fluid conduits or organ's arteries. Multiple microsensors may also be employed, e.g., a temperature probe disposed in close proximity to a pH probe, disposed in close proximity to a flow probe, etc. In this way several characteristics may be measured in a short length of fluid conduit by multiple sensors. Typically, the upstream sensors are placed just upstream of the organ so as to best measure the perfusate characteristics within the perfused organ. Microsensors may be placed within the main artery of the perfused organ in some applications.

The upstream sensor generates signals representative of the measured characteristics. The signals may be analog or digital. The signals are transmitted to a decoding device which can display the characteristics in real time, store the signals for future analysis, or both. Typically the signals are transmitted to a computer. When the upstream sensor transmits analog signals, an analog/digital converter may be interspaced between the sensor and the computer to convert the analog signals to digital signals. The computer may also generate inputs in response the signals. The inputs may then be transmitted to the pump speed control mechanism to alter or regulate the pump speed and hence control the mode of perfusion. Other inputs generated by the computer can be transmitted to the oxygenator to control the gas content of the perfusate, to the heat exchanger to control the temperature of the perfusate, and the electronic valve to control the chemical composition of the perfusate. Software is commercially available which provides these functions, such as Lab Windows®, produced by National Instruments of Austin, Tex., which can also be customized by the producer to meet individual needs.

After the perfusate leaves the second fluid conduit, it travels through the circulatory system of the organ. The organ may be contained in an organ chamber. The organ chamber may be environmentally controlled if appropriate. The organ may also be immersed in the perfusate or another solution the organ chamber. Immersion in a solution provides a means to more precisely control organ temperature and fluid balance. The solution may be static or flow over the organ such as described in U.S. Pat. No. 4,395,492, incorporated herein by reference.

As the perfusate flows through the organ's circulation, it is gathered by the venous system and exits an organ vein, e.g., the human renal vein. The perfusate may openly drain from the organ or channeled into a third fluid conduit. The third fluid conduit may include a downstream sensor similar to the upstream sensor. The perfusate characteristics measured by the downstream sensor can indicate functional and metabolic attributes of the organ. For example, if a kidney is being perfused, the Na and Cl concentrations and the osmolality can provide an indication of the perfusion and viability of the kidney since the renal cortex will filter electrolytes and alter the composition of the perfusate when the kidney is viable and fully perfused. When the kidney is ischemic, intra-renal circulatory shunts occur which alter the function of the kidney and hence the outflowing perfusate. Likewise, ischemia in a perfused heart can be detected by an increase in the lactate concentration of the outflowing perfusate.

The downstream sensor will generate signals representing the measured perfusate characteristics and transmit the signals to a decoding device. The decoding device will typically be a computer which can produce inputs in response to the signals. The inputs can be transmitted to the pump, oxygenator, or electronic valve as above. The downstream sensor generally is located just downstream of the organ. When microsensors are employed, the downstream sensor may be placed within the primary vein of the perfused organ. Because organ function will generally be monitored by a downstream sensor in the third fluid conduit, this provides the most accurate measure of the perfusate as it leaves the organ.

The third fluid conduit may empty the perfusate into disposal system appropriate for the particular application. Alternatively, the third conduit may channel the perfusate back to the source of a perfusate for recycling. In this case, the third conduit will generally include a filter, such as a as on Whatman 6702-3600, Gilman Filta 12158 or the like, to remove contaminants or cells from the perfusate. The third conduit may also include a downstream pump to propel the fluid to the source of the perfusate. The recycled perfusate will typically be returned directly to the mixing means, although the fluid can be returned to a reservoir.

Different components of devices of the present invention may be disposable. For example, the fluid conduits may be standard tubing employed for intravenous therapy. At least one fluid reservoir may be a commercially available container of intravenous fluid such as normal saline. Other disposable components will be readily appreciated by persons of skill in the art. Disposable components will be especially useful for therapeutic applications.

Also provided are devices for the simultaneous perfusion of multiple organs comprising one or more upstream pumps equal in number to the number of individual organs being simultaneously perfused, one or more first fluid conduits connecting each pump to a source of a perfusate, and one or more second fluid conduits connecting the arterial system of each individual organ with a single upstream pump, wherein each upstream pump is connected to only one organ. Generally, the organs are perfused from a single source of perfusate. This provides a means to perfuse each different organ with identical perfusate or with perfusates differing in only one characteristic or component. Generally the device will be capable of perfusing two organs, although this is not critical and may vary. Each organ is supplied with perfusate propelled by separate pumps. The pump speed of each pump is controlled by separate pump speed control mechanisms so that the pump speed of each pump may be controlled independently from each of the other pumps. The pumps may independently operate in either constant pressure mode or constant flow rate mode. The perfusion pressure or the perfusion flow rate to each organ may be independently regulated by this means.

In embodiments providing for the perfusion of multiple organs, the second fluid conduit is branched. The second fluid conduit has a single proximal end connected to the source of a perfusate. Distal to the second fluid conduit's proximal end, the second fluid conduit branches into multiple passages so that each passage fluidly connects the branch point to each separate pump thereby connecting each pump to the source of the perfusate. Each multiple passage may include an oxygenator or heat exchanger so that the temperature, pH, $pO_2$, $pCO_2$, and the like may be independently regulated to each pump and thus to each organ. In this manner it is possible to vary one characteristic of the perfusate and study the effect of that variation on organ function.

Methods for perfusing organs employing devices which can regulate both the perfusate flow rate or the perfusion pressure are also provided. Multiple organs may be simultaneously perfused on a single device by the disclosed methods. The methods generally comprise connecting the arterial system of each organ to separate pumps by means of at least one fluid conduit, which pumps are connected to a source of a perfusate and administering the perfusate to each organ by independently regulating each pump to adjust the pressure or flow rate of the perfusate in the fluid conduit.

A number of third fluid conduits are hermetically attached to the arterial system of each organ to be perfused. The conduits will generally be occlusive vascular catheters, although this is not critical. The fluid conduits provide a means to deliver the perfusate to the organ without fluid loss or contamination.

The perfusate flow through the second fluid conduit and into the each organ is regulated by a pump. The pump speed controls the flow rate of the perfusate. The flow rate is constant when the pump speed is constant. The pump speed also contributes to the pressure of the perfusate in the second fluid conduit. At a constant vascular resistance within an organ, the pump speed is directly proportional to the perfusate pressure. Thus, by altering the pump speed the perfusate pressure can be altered. The pump speed may be regulated by an operator to provide for constant perfusate flow rate or a constant perfusion pressure. Alternatively, the pump speed may be regulated by a computer that receives signals from sensors that monitor characteristics of the perfusate. As the perfusate flow rate or perfusate pressure are monitored, the pump speed can be adjusted by the computer to maintain consistency or introduce desired alterations in perfusate flow rate or perfusate pressure.

Methods for perfusing organs so as to optimize the viability of the perfused organs are also provided. The organ to be perfused is connected to a third fluid conduit and pump as above. The third fluid conduit has a downstream sensor which measures different characteristics of the perfusate exiting the organ, such as pH, temperature, glucose concentration, $pO_2$, and the like. The downstream sensor generates signals representing the measured characteristics. Typically the signals are transmitted to a computer. The signals may be decoded and displayed for the operator. The signals may also be analyzed by the computer and compared to predetermined values. The computer can generate inputs in response to the comparison of the signals to the predetermined values. The inputs may be transmitted to a mixing means, an oxygenator, a heat exchanger or the pump connected to the organ to alter the characteristics of the perfusate entering the organ. In this manner, organ viability can be optimized by prompt detection and correction of metabolic or functional abnormalities of the organ.

Methods for determining the effect of a test substance on an organ are also provided. At least two organs are perfused on a perfusion device of the present invention. One organ is exposed to the test substance by introducing the test substance into the perfusate distal to the pump. Because each organ is perfused by a separate pump, the test substance may be administered to only one organ when introduced to the perfusate downstream of the branch point in the second fluid conduit. If the test substance is introduced upstream to the upstream sensor, the concentration of the substance entering the test may also be determined. The effect on the test organ may be determined by comparing the characteristics of the perfusate leaving the test organ to those of the perfusate leaving the control organ as measured by downstream sensors. Alternatively, the effect of the substance on the test organ can be measured by means other than the characteristics of the perfusate leaving the organ, such as an intraventricular balloon to measure cardiac wall tension or contractility.

Referring now to FIG. 1, there is shown a schematic illustration of one embodiment of a perfusing device constructed in accordance with the principles of the present invention. Like reference characters will be used to indicate like elements.

The illustrated embodiment is a device for simultaneously perfusing two organs. Multiple reservoirs 1 are able to hold different solutions. The solutions flow through individual tubing 2 from the reservoirs 1 to an electronic valve 3. The electronic valve 3 regulates the flow of each different solution into a common tube 4 thereby producing the perfusate. The composition of the perfusate may be altered by changing the ratio of the flow rates of the different solutions through the electronic valve 3. As the perfusate flows through the common tube 4 it is filtered by a filter 5. Following filtration, the perfusate continues through the common tube 4 and through an oxygenator 6. The oxygenator regulates the $pO_2$ and $pCO_2$ in the perfusate by means of exposing the perfusate to a mixture $O_2$ and $CO_2$ from a gas source 7. Upon leaving the oxygenator 6, the perfusate continues through the common tube 4 into a heat exchanger 8. The heat exchanger 8 regulates the temperature of the perfusate. After exiting the heat exchanger 8 the perfusate enters a first fluid conduit 9. The first fluid conduit 9 is comprised of a common first fluid conduit 10 and branched first fluid conduits 11. The perfusate which flows into each of the branched conduits 11 is identical. The perfusate then flows into upstream pumps 12 which pumps perfusate away from the reservoirs 1 and toward the organs 15 located in organ chambers 25. The perfusate is pumped into second fluid conduits 13. The upstream pumps 12 can regulate the pressure of the perfusate in the second fluid conduits 13 or the flow rate of the perfusate through the second fluid conduits 13. Characteristics of the perfusate are measured by an upstream sensor 14 located in the second fluid conduit 13. The upstream sensor 14 is located just upstream of the perfused organs 15 so that the measured perfusate characteristics will closely approximate the characteristics of the perfusate entering the organs 15. After the perfusate has flowed through the organs 15 the perfusate flows into a third fluid conduit 16. The perfusate is pumped by a downstream pump 17 away from the organs 15. The third fluid conduits 16 channel the perfusate back to the electronic valve 3 for re-use. Previously circulated perfusate flows through a filter 18 before reaching the electronic valve 3.

A computer 19 receives signals generated by the upstream sensors 14. The upstream sensors 14 produce signals representing each of the measured characteristics. The computer 19 may store the signals for future use, display the signals to the operators on a terminal display 20, or analyze the signals and produce inputs in response thereto. The inputs produced by the computer 19 in response to the signals from the upstream sensors 14 representing the pH, $pO_2$, or $pCO_2$ may be transmitted to the gas source 7 to alter the gas mixture contacting the perfusate. In this manner, any of these characteristics may be regulated in the perfusate which is entering the organs 15.

The inputs produced by the computer 19 in response to signals from the upstream sensors 14 representing the temperature of the perfusate may be transmitted to the heat exchanger 8 to alter the temperature of the heat exchanger 8. The temperature of the perfusate entering the organs 15 may be adjusted in this manner.

The inputs produced by the computer 19 in response to the perfusion pressure or flow rate of the perfusate in the second fluid conduits 13 may be transmitted to upstream pump speed control mechanisms 21. The pump speed control mechanisms 21 control the speed of the upstream pumps 12. The speed of the upstream pumps 12 may be controlled independently. The computer may produce inputs which will cause the pump speed control mechanisms 21 to vary the speed of the upstream pumps 12 to regulate the perfusion pressure or the perfusate flow rate in the second fluid conduits 13 by controlling the pump speed.

An injection port 24 is located in one of the second fluid conduits 13. The injection port 24 allows for selective administration of test compound, such as a pharmaceutical, toxin, hormone, or other substance, into only one of the organs 15. The injection port is located upstream to the sensor 14 in the second fluid conduit 13. The sensor 14 may determine concentrations of the test substance in the perfusate. The single injection port 21 located downstream from the common first fluid conduit 10 provides a method of perfusing two organs 15 with a perfusate identical in all respects except the added test substance. In this manner, accurate determination of the effect of the test substance on the organ 15 is possible.

Figure 2:
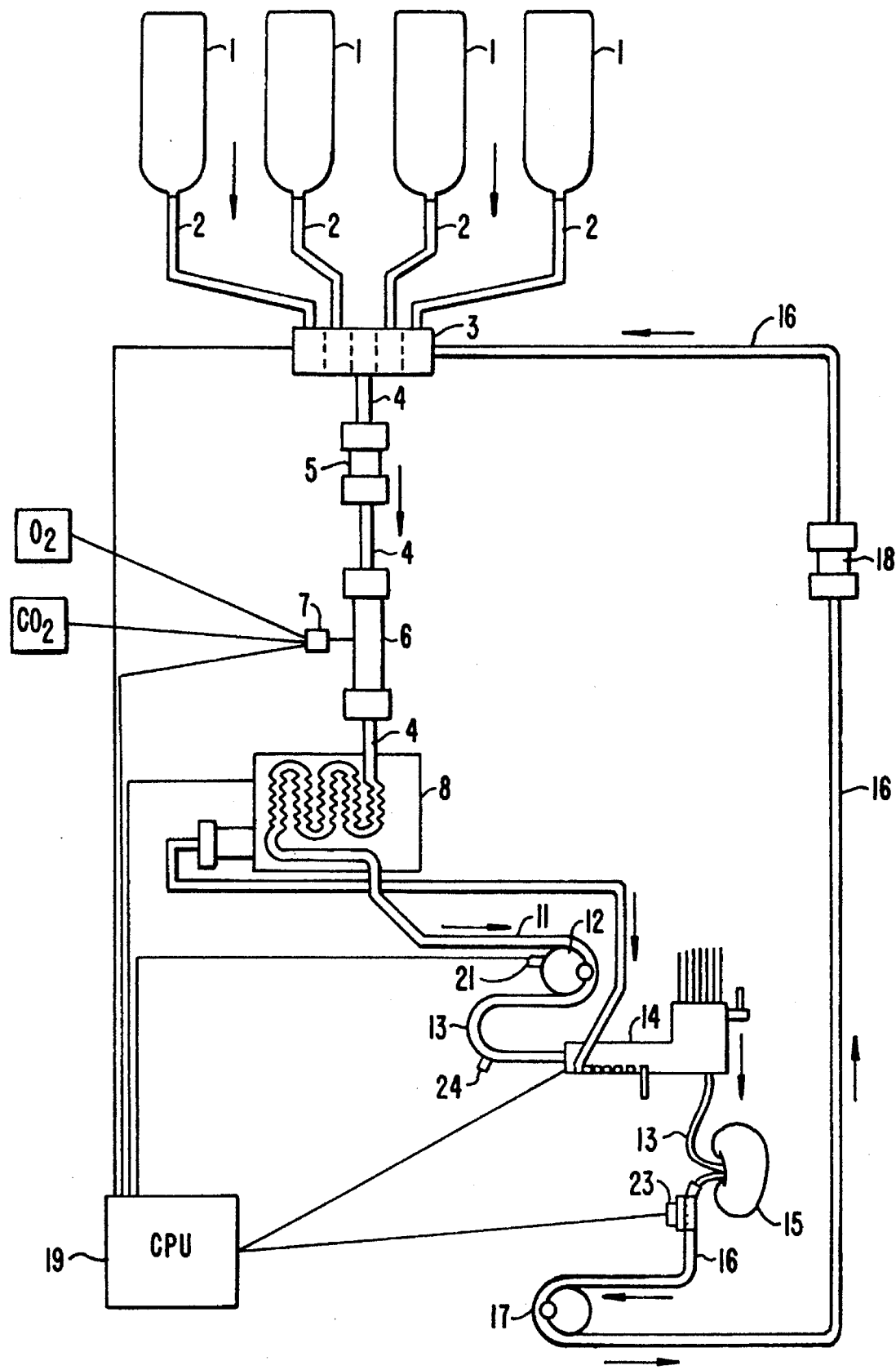
FIG. 2 illustrates a schematic diagram of a perfusion device capable of altering perfusion characteristics so as to optimize organ viability for perfusing a single organ constructed in accordance with the principles of the present invention.

Referring now to FIG. 2, a perfusion device for perfusing a single organ constructed in accordance with the principles of the present invention is illustrated. The embodiment in FIG. 2 monitors characteristics of the perfusate as it flows from the organ. As the characteristics are monitored, the temperature, gas content, chemical composition, of the perfusion pressure, or flow rate perfusate flowing into the organ can be altered in response to the characteristics measured in the perfusate flowing out of the organ.

Multiple reservoirs i may contain different solutions. The solutions flow through tubing 2 into an electronic valve 3. The electronic valve 3 mixes the solutions in controlled ratios to produce a perfusate with specific characteristics. The electrolyte concentration, glucose concentration, pH, etc. may be controlled by the electronic valve 3.

Following mixing of the perfusate in the electronic valve 3, the perfusate flows into a common tubing 4. The perfusate flows through a filter 5 and into an oxygenator 6. The oxygenator 6 contacts the perfusate with a mixture of $O_2$ and $CO_2$. The mixture ratio of $O_2$ and $CO_2$ is controlled by a gas source 7. After passing through the oxygenator 6, the perfusate continues through the common tubing 4 and into a heat exchanger 8. The heat exchanger 8 regulates the temperature of the perfusate.

After following through the heat exchanger 8, the perfusate flows through the first fluid conduit 11. The perfusate goes through an upstream pump 12 which propels the perfusate away from the heat exchanger 8. The perfusate is pumped into the second fluid conduit 13. An injection port 21 is located in the second fluid conduit 13 to enable the operator to administer a pharmaceutical, hormone or the like to the organ 15. The perfusate flows into a first sensor 14 which can monitor a plurality of characteristics of the perfusate. The perfusate then flows into the organ 15. After circulating through the organ 15, the perfusate flows into the third fluid conduit 16. A downstream sensor 23 monitors characteristics of the perfusate as the perfusate leaves the organ 15. The perfusate is pumped by a downstream pump 17 through a filter 18 and back into the electronic valve 3. The electronic valve 3 can mix the returning perfusate with solutions from the reservoirs 1 to recycle the perfusate.

The upstream sensor 14 and the downstream sensor 23 produce signals representative of the perfusate characteristics which are monitored. The signals are transmitted to a computer 19. The computer 19 may display the information represented by the signals in real time, store the information represented by the signals, or produce inputs in response to the signals. The inputs may control the gas source 7, heat exchanger 8, pump speed control mechanism 21 and/or electronic valve 3. Because the inputs are produced and varied by the computer 19 in response to the signals produced by the upstream sensor 14 and the downstream sensor 23, the computer 19 may adjust the composition and other physical characteristics of the perfusate to optimize organ viability.

The foregoing is offered primarily for purposes of illustration. It will be readily apparent to those of skill in the art that the components of the perfusion devices, the methods of organ perfusion, and other characteristics of the invention described herein may be modified or substituted in various ways without departing from the spirit and scope of the invention.

What is claimed is:

1. A method of perfusing at least one organ with a perfusate to maintain organ viability comprising:

connecting the arterial system of each organ to separate pumps by means of at least one fluid conduit, which pumps are connected to a source of a perfusate, each of said pumps having a pump speed that is independently and selectively controlled to regulate perfusate pressure and perfusate flow rate; and administering the perfusate to each organ by independently regulating each pump to selectively adjust the pressure and flow rate of the perfusate in the fluid conduit.

2. The method of claim 1, wherein a first organ and a second organ are perfused.

3. The method of claim 2, wherein the effect of a test substance on an organ is determined by exposing the first organ to the test substance while being perfused, isolating the second organ from the test substance, and detecting differences in a functional attribute of the first and second organs.

4. The method of claim 1, wherein a first sensor monitors characteristics of the perfusate in the fluid conduit and produces signals representing the monitored characteristics.

5. The method of claim 4, wherein the first sensor monitors the pressure and flow rate of the perfusate in the fluid conduit and regulates the pump thereby.

6. The method of claim 1, wherein a second sensor monitors a characteristic of the perfusate exiting the venous system of each organ and produces a signal thereby.

7. The method of claim 6, wherein the perfusate is altered in composition, pressure or flow rate in the fluid conduit in response to the signal.

8. The method of claim 6, wherein the signal is transmitted to a computer which produces an input representing the signal.

* * * * *